(12) United States Patent
Artaria et al.

(10) Patent No.: US 8,632,826 B2
(45) Date of Patent: Jan. 21, 2014

(54) COSMETIC WRINKLE TREATMENT METHOD BASED ON A ZANTHOXYLUM BUNGEANUM EXTRACT

(75) Inventors: Christian Artaria, Milan (IT); Giada Maramaldi, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 13/202,683

(22) PCT Filed: Feb. 18, 2010

(86) PCT No.: PCT/EP2010/001010
§ 371 (c)(1), (2), (4) Date: Oct. 6, 2011

(87) PCT Pub. No.: WO2010/094477
PCT Pub. Date: Aug. 26, 2010

(65) Prior Publication Data
US 2012/0021082 A1 Jan. 26, 2012

(30) Foreign Application Priority Data
Feb. 23, 2009 (IT) .............................. MI2009A0247

(51) Int. Cl.
*A61K 36/00* (2006.01)
*A61K 36/758* (2006.01)
(52) U.S. Cl.
USPC .......................................... 424/725; 424/777

(58) Field of Classification Search
None
See application file for complete search history.

(56) References Cited

U.S. PATENT DOCUMENTS 6,419,950 B2 * 7/2002 Bombardelli et al. ........ 424/452
6,423,325 B1 7/2002 Alaluf et al.

FOREIGN PATENT DOCUMENTS

| JP | 2003342184 A | * 12/2003 |
| JP | 2008-13461 A | 1/2008 |
| WO | WO 00/02570 A1 | 1/2000 |

OTHER PUBLICATIONS

Database WPI, Week 200404, Thomson Scientific, London, GB; AN 2004-039663.
"Abstracts for the International Investigative Dermatology 2008" Journal of Dermatological Science, Apr. 1, 2008, vol. 50, No. 2, Elsevier Science Publishers, Shannon, IR.
Database WPI, Week 200241, Thomson Scientific, London, GB; AN 2002-379876.

* cited by examiner

*Primary Examiner* — Qiuwen Mi
(74) *Attorney, Agent, or Firm* — Arent Fox LLP

(57) ABSTRACT

The present invention relates to a cosmetic wrinkle treatment method which comprises the topical application of a *Zanthoxylum bungeanum* extract obtainable by extraction with carbon dioxide under hypercritical conditions. The present invention also relates to the use of such *Zanthoxylum bungeanum* extract for the preparation of topical compositions for the cosmetic treatment of skin wrinkles.

4 Claims, No Drawings

COSMETIC WRINKLE TREATMENT METHOD BASED ON A ZANTHOXYLUM BUNGEANUM EXTRACT

CROSS-REFERENCE TO RELATED APPLICATION

This application is a National Stage entry of International Application No. PCT/EP2010/001010, filed Feb. 18, 2010, which claims priority to Italian Patent Application No. MI2009A000247, filed Feb. 23, 2009 the disclosure of the prior applications are incorporated in its entirety by reference.

The present invention relates to a cosmetic wrinkle-treatment method which comprises the topical application of a *Zanthoxylum bungeanum* extract obtainable by extraction with carbon dioxide under hypercritical conditions.

The present invention also relates to the use of such *Zanthoxylum bungeanum* extract for the preparation of topical compositions for the cosmetic treatment of skin wrinkles.

TECHNICAL BACKGROUND

The pericarp of *Zanthoxylum bungeanum* is commonly used in China as a food spice. This part of the plant is also used in Chinese and Indian traditional medicine as a local anaesthetic and to treat dysentery. The essential oil, which contains a series of monoterpenes including 1,8 cymene, linalool, 4-terpinol, caryophyllene, limonene, etc., is reported to be a potent insect repellent.

The antiviral activity of the peel of said fruit was recently described in EP 568001.

In U.S. Pat. No. 5,137,912, chelcrythrine, extracted from the root bark of *Zanthoxylum simulans* (a synonym of *bungeanum*), was found to be active in the prevention of thrombosis. As described in JP 01294657, extraction from the pericarp with organic solvents allows the preparation of an extract containing isobutylamides which possesses local anaesthetic activity that is already present 30 seconds after application to the tongue, and persists for 20-80 minutes.

DESCRIPTION OF THE INVENTION

It has now surprisingly been found that *Zanthoxylum bungeanum* pericarp extract, prepared by extraction with carbon dioxide under hypercritical conditions, possesses significant anti-wrinkle activity.

The present invention therefore relates to a cosmetic wrinkle-treatment method based on said *Zanthoxylum bungeanum* extract, as well as to the use of such *Zanthoxylum bungeanum* extract for the preparation of topical compositions for the cosmetic treatment of skin wrinkles.

The process for the preparation of said extract is described in patent EP 1 096 944, filed by the Applicant, and involves extraction from the pericarp of *Zanthoxylurn bungeanum*, finely ground or transformed into pellets, with carbon dioxide under pressure conditions ranging from 150 to 300 bars, preferably 180-230 bars, at temperatures ranging from 35 to 55° C., preferably at 35-40° C. The resulting extract can either be used as it is, after removing the extraction water, or further purified by partitioning it with immiscible solvents such as aliphatic alcohols and aliphatic hydrocarbons, preferably n-hexane or petroleum ether.

The pharmacological tests to which the extract thus obtained has been subjected demonstrate a marked anti-wrinkle activity; it is therefore useful in the cosmetic field in all skin treatments for which an anti-wrinkle action is required. The invention can be implemented using the extract at concentrations of 0.1 to 0.5% or using a 20% solution of the extract in oleyl-alcohol, commercially available under the name Zanthalene®, at a concentration between 0.5 and 2%.

The formulations according to the invention will be prepared according to well-known conventional methods such as those described in "Remington's Pharmaceutical Handbook", Mack Publishing Co., N.Y., USA, together with suitable excipients. Examples of formulations according to the invention include creams, ointments, powders, lotions and the like.

Pharmacological Tests

The purpose of the study was to evaluate the short-term face-lifting effect of the active ingredient.

The trial was conducted on 14 healthy Caucasian female volunteers aged 35 to 65, who were not taking any topical or systemic drugs liable to affect the results of the test, did not suffer from any skin disease, and presented wrinkles in the periocular area. The volunteers were instructed not to use products other than those tested, or to undergo UV radiation, throughout the study.

Materials and Methods

Negative casts of the skin surface were taken with an adhesive disc and a quick-setting synthetic polymer (SILFO—Flexico Ltd., UK). The adhesive disc was placed on the volunteer's skin to demarcate the test area and prevent the skin from stretching during application of the polymer. A small amount of polymer was then distributed over the inner circular area of the disc and left in situ for a few minutes, until dry. The disc was then removed, and an exact copy of the skin was thus obtained.

The skin casts were then analysed with image-processing software (Quantilines, Monaderm) which allows global analysis of the data for the main parameters, according to the method described by Corcuff (P. Corcuff, J. L. Lévêque "Skin Surface Replica Image, Analysis of Furrows and Wrinkles" in: "Handbook of Non-Invasive Methods and the Skin", Serup and Jermec Eds. CRC Press; pp. 89-96).

The software measures the average roughness (Ra), and the reduction in said value represents the index of anti-wrinkle efficacy.

Evaluation Method

The test was performed in a bioclimatic chamber (24±2° C.; 50±10% relative humidity) after a suitable acclimatisation period. Casts of the periocular skin area on both sides of the face were taken at the beginning of the test.

Two products were tested on the periocular areas, each according to the following study protocol:

Side A: 1% Zanthalene cream;
Side B: placebo.

Thirty minutes after the treatment, the anti-wrinkle activity was evaluated by taking further skin casts.

Mathematical Processing

The mean values and standard deviations were calculated for each control time (T0 and T30 min.) The variation in the parameter was also calculated:

$$T_{30} - T_0 = \text{Variation in parameter}$$

where: $T_{30}$=mean value at end of test
$T_0$=mean value at start of test
This difference is also shown as the percentage variation.

The initial and final values were compared by means of the t-test on paired samples. The differences between the data sets were deemed significant if probability p was≤0.05.

The results set out in the Table clearly demonstrate that the effect of the 1% Zanthalene® cream described in the example is significantly superior to that of the placebo cream (same formulation as in the example, less the active ingredient).

TABLE

|  | T0 mean ± sd | T30 min. mean ± sd | % variation | t-test |
|---|---|---|---|---|
| Placebo | 14.43 ± 4.38 | 14.49 ± 3.73 | +0.42% | p > 0.05 |
| 1% formulation | 16.07 ± 4.24 | 13.45 ± 3.09 | −16.30% | p < 0.05 |

The following is an example of a formulation according to the invention.

EXAMPLE

| Ingredient | Amount |
|---|---|
| Zanthalene ® | 1.00 g |
| Sodium EDTA | 0.10 g |
| Imidazolidinyl urea | 0.30 g |
| Polyacrylamide, C13-14 isoparaffin, Laureth-7 | 3.00 g |
| Oleyl alcohol | 6.50 g |
| Pentaerythrityl tetra-di-t-butyl hydroxyhydrocinnamate | 0.10 g |

-continued

| Ingredient | Amount |
|---|---|
| Diethylhexyl syringylidene malonate, caprylic/capric triglyceride | 0.10 g |
| Tocopherol | 0.20 g |
| Methyl paraben | 0.20 g |
| Water q.s. to | 100 g |

The invention claimed is:

1. A method for short-term face-lifting comprising administering topically a cosmetic composition consisting of an extract of *Zanthoxylum bungeanum*, wherein the extract of *Zanthoxylum bungeanum* is obtained by extracting the pericarp with hypercritical $CO_2$.

2. The method according to claim 1, wherein the extract of *Zanthoxylum bungeanum* is obtained by extracting the pericarp with hypercritical $CO_2$ at temperatures between 35 and 55° C., and pressures between 150 and 300 bars.

3. A method for treating wrinkles comprising administering topically a cosmetic composition consisting of an extract of *Zanthoxylum bungeanum*, wherein the extract of *Zanthoxylum bungeanum* is obtained by extracting the pericarp with hypercritical $CO_2$.

4. The method according to claim 3, wherein the extract of Zanthoxylum bungeanum is obtained by extracting the pericarp with hypercritical $CO_2$ at temperatures between 35 and 55° C., and pressures between 150 and 300 bars.

* * * * *